United States Patent [19]

Hsieh

[11] Patent Number: 5,515,409
[45] Date of Patent: May 7, 1996

[54] HELICAL INTERPOLATIVE ALGORITHM FOR IMAGE RECONSTRUCTION IN A CT SYSTEM

[75] Inventor: Jiang Hsieh, Waukesha, Wis.

[73] Assignee: General Electric Company, Milwaukee, Wis.

[21] Appl. No.: 362,247

[22] Filed: Dec. 22, 1994

[51] Int. Cl.$^6$ ........................................ A61B 6/03
[52] U.S. Cl. ........................ 378/15; 364/413.16
[58] Field of Search .................. 364/413.16; 378/15, 378/94

[56] References Cited

U.S. PATENT DOCUMENTS

| | | | |
|---|---|---|---|
| 4,789,929 | 12/1988 | Nishimurs et al. | 364/413.13 |
| 5,090,037 | 2/1992 | Toth et al. | 378/4 |
| 5,208,746 | 5/1993 | King et al. | 364/413.16 |
| 5,216,601 | 6/1993 | Crawford et al. | 364/413.16 |
| 5,233,518 | 8/1993 | King et al. | 364/413.18 |
| 5,265,142 | 11/1993 | Hsieh | 378/4 |
| 5,270,923 | 12/1993 | King et al | 364/413.13 |
| 5,291,402 | 3/1994 | Pfoh | 364/413.14 |
| 5,408,511 | 4/1995 | Grangeat et al. | 378/19 |

OTHER PUBLICATIONS

C. R. Crawford, K. F. King, Computed Temography Scanning with Simultaneous Patient Translation, Med. Phy. 17(6) Nov./Dec. 1990.

*Primary Examiner*—David P. Porta
*Assistant Examiner*—David Vernon Bruce
*Attorney, Agent, or Firm*—John S. Beulick; John H. Pilarski

[57] ABSTRACT

The present invention, in one form, is an apparatus for performing image reconstruction using data obtained by a helical scan. In reconstructing an image in accordance with the present invention, projection data arrays corresponding to data planes associated with the slice to be imaged are generated. Weighting factors are then applied to the data arrays to assign a weight to each particular data element thereby creating a weighted projection data array. The weighted projection data array is then filtered and back projected to create an image data array from which an image slice is generated. In accordance with the present invention, the weighting function used in creating the weighted projection data array is based upon a plane of reconstruction which is not necessarily perpendicular to the z-axis.

6 Claims, 4 Drawing Sheets

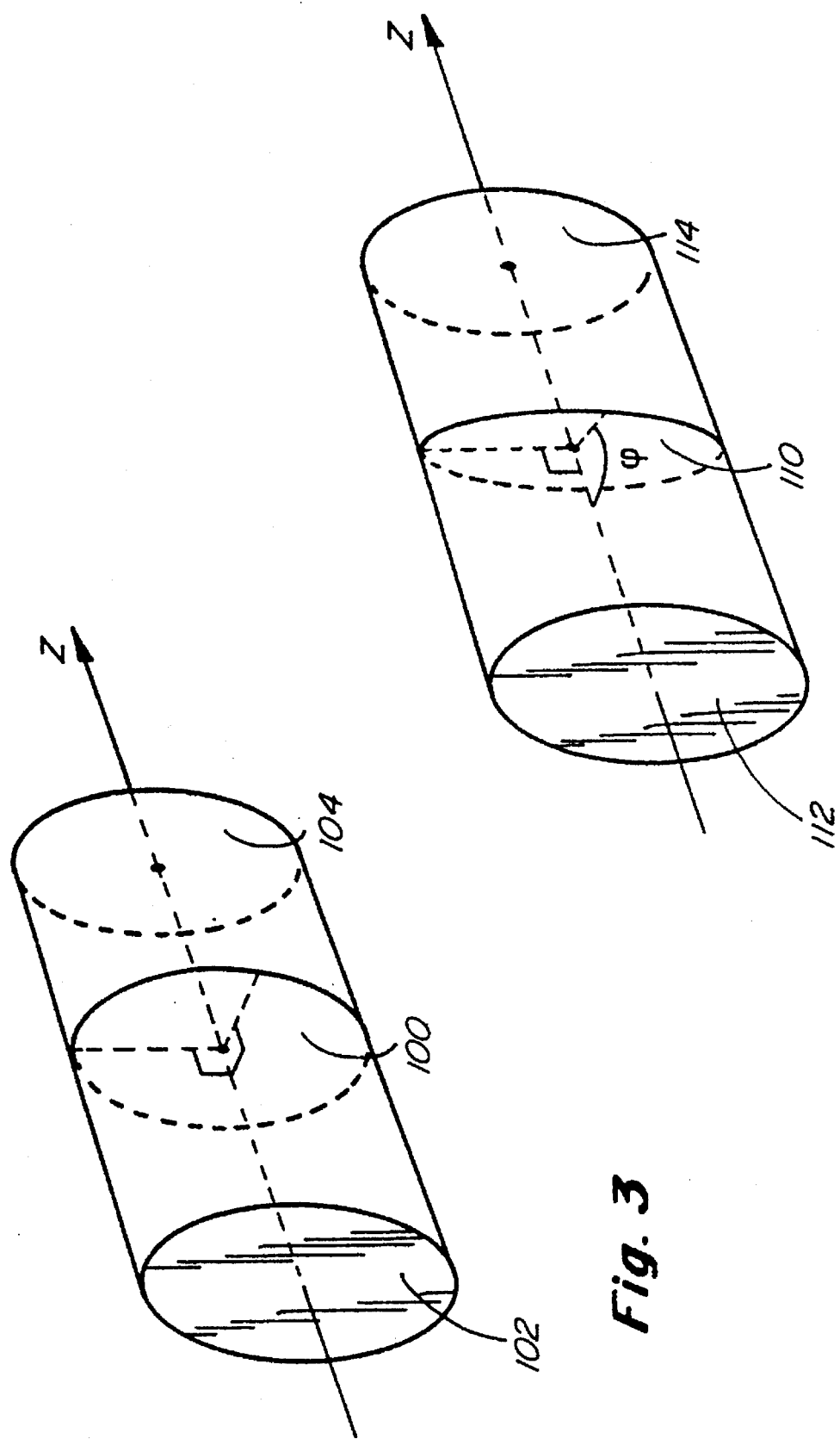

HELICAL INTERPOLATIVE ALGORITHM FOR IMAGE RECONSTRUCTION IN A CT SYSTEM

FIELD OF THE INVENTION

This invention relates generally to computed tomography (CT) imaging and more particularly, to an interpolative algorithm for reconstructing images from projection data acquired from a helical scan.

BACKGROUND OF THE INVENTION

In CT systems, an x-ray source projects a fan-shaped beam which is collimated to lie within an X-Y plane of a Cartesian coordinate system, termed the "imaging plane". The x-ray beam passes through the object being imaged, such as a patient, and impinges upon a linear array of radiation detectors. The intensity of the transmitted radiation is dependent upon the attenuation of the x-ray beam by the object. Each detector of the linear array produces a separate electrical signal that is a measurement of the beam attenuation. The attenuation measurements from all the detectors are acquired separately to produce a transmission profile.

The x-ray source and the linear detector array in a CT system are rotated with a gantry within the imaging plane and around the object so that the angle at which the x-ray beam intersects the object constantly changes. A group of x-ray attenuation measurements from the detector array at one gantry angle is referred to as a "view". A "scan" of the object comprises a set of views made at different gantry angles during one revolution of the x-ray source and detector. In an axial scan, data is processed to construct an image that corresponds to a two dimensional slice taken through the object. One method for reconstructing an image from a set of data is referred to in the art as the filtered back projection technique. This process converts the attenuation measurements from a scan into integers called "CT numbers" or "Hounsfield units", which are used to control the brightness of a corresponding pixel on a cathode ray tube display.

Computed tomograph scans have been acquired with a stop-and-shoot technique. With the stop and shoot method, a complete set of projections is acquired before the patient is translated to a next location. To ensure image quality, a non-zero inter-scan delay (ISD) is introduced between scans. The ISD is typically long enough to ensure that the gantry rotates at a constant speed while obtaining projection data and that the patient moves to the next location and stops before a next scan is initiated. At least with respect to patient throughput, this mode of scanning is not efficient.

CT scans also may be acquired using a continuous data acquisition technique. In this mode, both the gantry and the patient move at a constant speed. The data acquisition is continuous throughout the entire process. This scanning mode is known as a helical or spiral scan.

Although helical scanning has many advantages (e.g., arbitrary location image reconstruction and improved patient throughput), there also are some disadvantages. For example, a basic assumption of tomographic reconstruction theory assumes that each projection in a data set represents line integrals of the same object. That is, the distribution of the attenuation map remains unchanged in the reconstruction plane. When a non-homogeneous object is scanned in the helical mode, the object is constantly translated during the data acquisition. Due to the heterogeneity of the object, the attenuation distribution inside the scanning plane changes constantly. These continuous changes clearly violate the basic assumption of the tomographic reconstruction theory. If the projection data is not properly corrected for the object translation, undesirable image artifacts will result.

Various correction algorithms to address the heterogeneity issue are known. For example, a helical extrapolative (HE) algorithm is described in U.S. Pat. No. 5,233,518 which is assigned to the present assignee. The HE algorithm is based upon the fact that each set of helical projections can be divided into two sets of half scans. By performing interpolation and extrapolation, a more consistent set of projections at a predefined slice plane can be obtained. Due to the nature of the fan beam geometry, the weighting function derived from the algorithm is not continuous along a line in Radon space. To avoid any artifacts caused by this discontinuity, a feathering algorithm which ensures a smoother transition between the two regions is employed. The nature of the extrapolation also produces weights that are negative or greater than one.

It would be desirable to provide an interpolative algorithm which is more stable than its extrapolative counterpart. In addition it would be desirable to eliminate a need for a feathering algorithm to ensure an artifact free reconstruction and to improve the noise characteristics of such reconstruction.

SUMMARY OF THE INVENTION

In reconstructing an image slice in accordance with one form of the present invention, a projection data array is created. Once the array is created, the data elements within the array are assigned weights. The weighted data is then used to created a weighted projection data array. Using the weighted projection data array, the data is filtered and back projected. An image data array is created as a result of the filtering and back projection.

The weighting function applied to create the weighted projection data array is:

$$w(\beta,\gamma) = \begin{cases} \dfrac{\beta}{\pi - 2\gamma} & 0 \leq \beta \leq \pi - 2\gamma \\ \dfrac{2\pi - \beta}{\pi + 2\gamma} & \pi - 2\gamma < \beta \leq 2\pi \end{cases}$$

As set forth below in more detail, the present algorithm provides improved performance in image generation by providing improved noise suppression and in eliminating a need for a feathering algorithm due to discontinuities.

BRIEF DESCRIPTION OF THE DRAWINGS

FIG. 3 illustrates a plane of reconstruction half-way within the data projection set.

FIG. 4 illustrates a tilted plane of reconstruction.

DETAILED DESCRIPTION OF THE DRAWINGS

Figure 1:
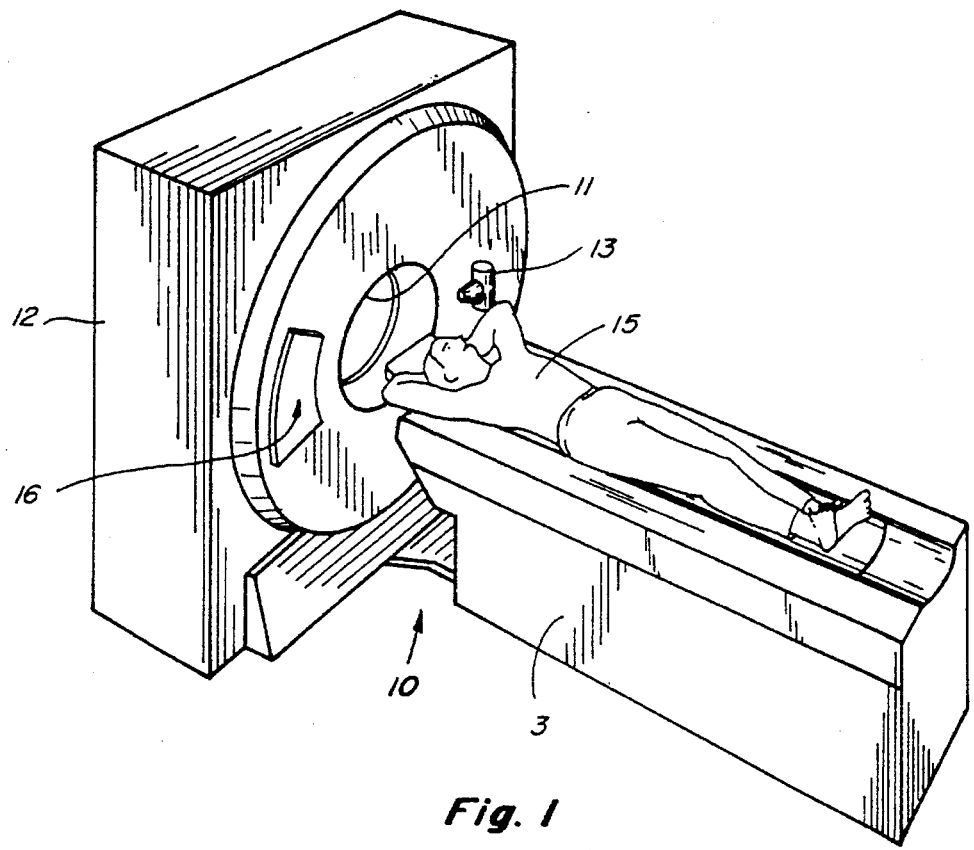
FIG. 1 is a pictorial view of a CT imaging system in which the present invention may be employed.
Figure 2:
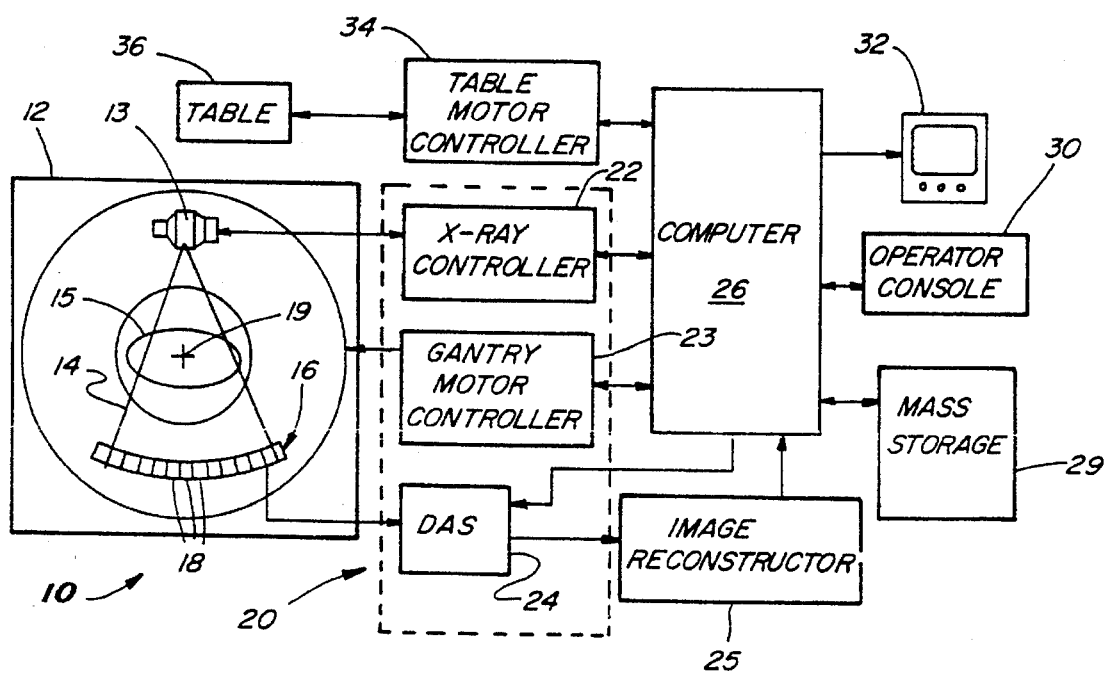
FIG. 2 is a block schematic diagram of the CT imaging system illustrated in FIG. 1.

With reference to FIGS. 1 and 2, a computed tomography (CT) imaging system 10 includes a gantry 12 representative of a "third generation" CT scanner. Gantry 12 has an x-ray source 13 that projects a beam of x-rays 14 toward a detector array 16 on the opposite side of gantry 12. Detector array 16 is formed by two rows of detector elements 18 which together sense the projected x-rays that pass through a medical patient 15. Each detector element 18 produces an electrical signal that represents the intensity of an impinging x-ray beam and hence the attenuation of the beam as it passes through patient 15. During a scan to acquire x-ray projection data, gantry 12 and the components mounted thereon rotate about a center of rotation 19.

Rotation of gantry 12 and the operation of x-ray source 13 are governed by a control mechanism 20 of CT system 10. Control mechanism 20 includes an x-ray controller 22 that provides power and timing signals to x-ray source 13 and a gantry motor controller 23 that controls the rotational speed and position of gantry 12. A data acquisition system (DAS) 24 in control mechanism 20 samples analog data from detector elements 18 and converts the data to digital signals for subsequent processing. An image reconstructor 25 receives sampled and digitized x-ray data from DAS 24 and performs high speed image reconstruction. The reconstructed image is applied as an input to a computer 26 which stores the image in a mass storage device 29.

Computer 26 also receives commands and scanning parameters from an operator via console 30 that has a keyboard. An associated cathode ray tube display 32 allows the operator to observe the reconstructed image and other data from computer 26. The operator supplied commands and parameters are used by computer 26 to provide control signals and information to DAS 24, x-ray controller 22 and gantry motor controller 23. In addition, computer 26 operates a table motor controller 34 which controls a motorized table 36 to position patient 15 in gantry 12.

In reconstructing an image slice, typically a projection data array is created. Once the array is created, the data elements within the array are assigned weights. The weighted data is then used to created a weighted projection data array. Using the weighted projection data array, the data is filtered and back projected. An image data array is created as a result of the filtering and back projection.

Referring to FIG. 3, and in using interpolative or extrapolative algorithms for reconstructing an image from projection data, the plane of reconstruction (POR) 100 is placed half-way within the projection data sets and is perpendicular to the axis of translation. By placing the POR 100 at the mid-point between two end projection planes (first 102 and last 104), the maximum error inherent in the projection data set will be minimized since the mid-plane 100 roughly divides the difference between the two extreme projections 102 and 104 by half. The requirement that the POR 100 be perpendicular to the z-axis has been carried over from the conventional axial scan geometry where the POR is always normal to the z-axis.

There is no logical reason, however, why the POR can not be selected at a different angle with respect to the z-axis. For example, the POR 100 can be selected such that the angle $\phi$ is less than 90 degree as shown in FIG. 4. For the purpose of illustration, angle $\phi$ in FIG. 4 is drawn significantly different from 90 degrees. In practice, however, since the first 112 and the last 114 projection planes are fairly close to each other, the amount of titling of the POR 110 is very small.

Figure 5B:
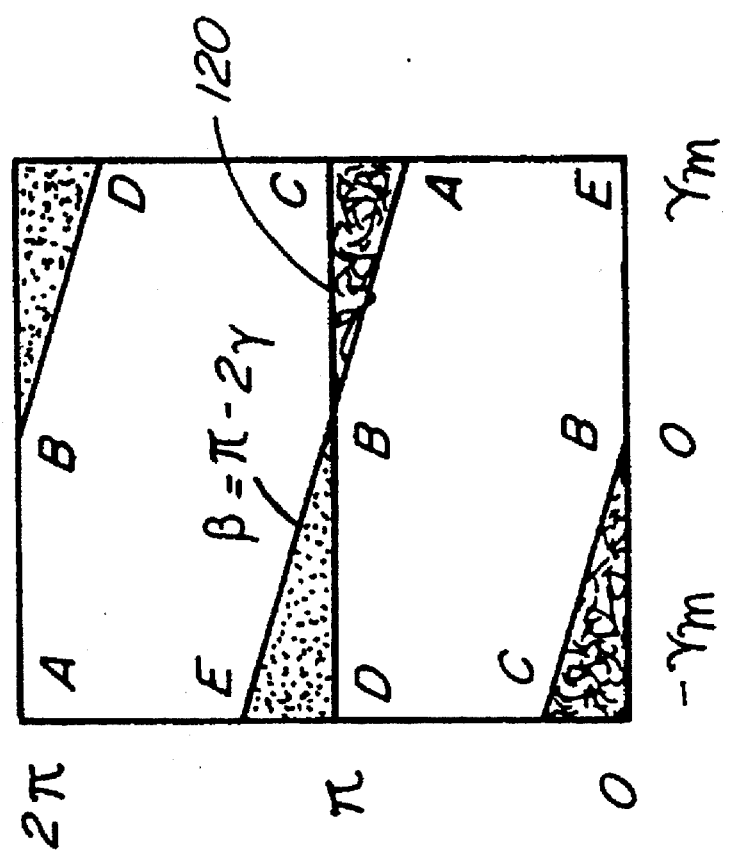
FIG. 5a illustrates a plane of reconstruction in Radon space and FIG. 5b illustrates a map of data redundancy in connection with the HE algorithm.
Figure 5A:
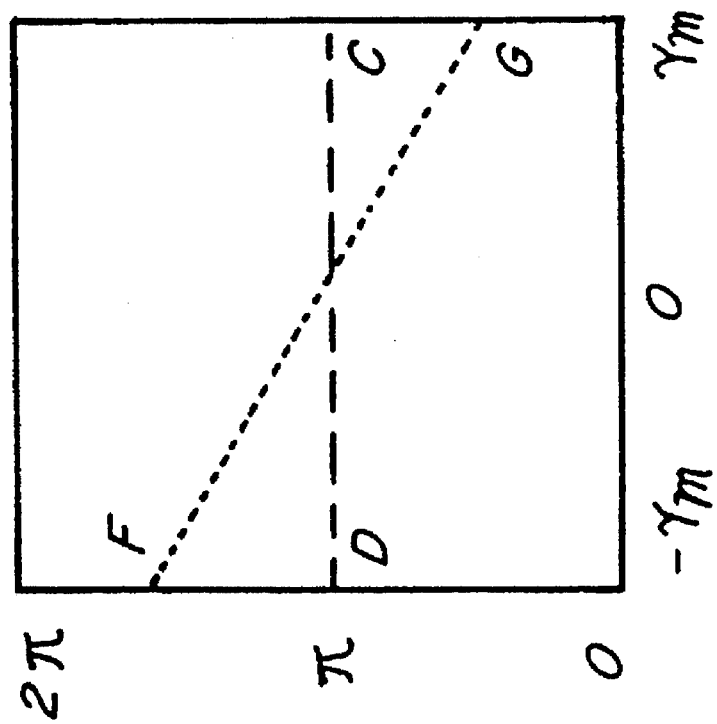

The impact of tilting the POR is shown in Radon space in FIG. 5a. Particularly, FIG. 5a shows a two dimensional plot of projections in Radon space with the horizontal axis representing the fan angle and the vertical axis representing the viewing angle. Line DC depicts a conventional POR 120 and is perpendicular to the axis of rotation. A reconstruction plane that is not normal to the z-axis is represented by a line FG. As the difference between angle $\phi$ and 90 degree increases, the line FG is tilted further away from the line DC.

With respect to the helical extrapolative (HE) algorithm, and for the ease of reference, a map of the data redundancy is shown in FIG. 5b. The corresponding redundant samples are labeled by the same letters. For example, the shaded triangle at the lower left hand corner (looking at the page) ABC is a duplication of the samples in the shaded middle triangle ABC. Since both samples are located on the same side of the POR (line DC), an extrapolative scheme is used. The resulting weighting function is given as:

$$w(\beta,\gamma) = \begin{cases} \dfrac{\beta + 2\gamma}{\pi + 2\gamma} & 0 \leq \beta \leq \pi - 2\gamma \\ \dfrac{2\gamma - \beta - 2\gamma}{\pi + 2\gamma} & \pi - 2\gamma < \beta \leq 2\pi \end{cases} \quad (1)$$

The function $w(\beta, \gamma)$ is discontinuous in $\gamma$ along the line $\beta = \pi - 2\gamma$. Also, $w(\beta, \gamma)$ in the two shaded triangles (ABC at the bottom and BDE at the top) becomes negative. To eliminate the discontinuity, $w(\beta, \gamma)$ is feathered across the line $\beta = \pi - 2\gamma$. The feathering of $w(\beta, \gamma)$ will destroy the property that the sum of the weights of the redundant samples equal to one.

Figure 6B:
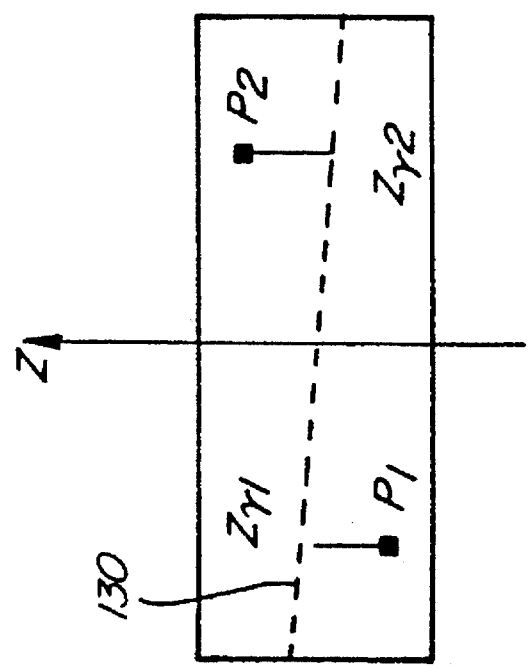
FIG. 6a illustrates redundant sample pairs of projection data points and FIG. 6b illustrates the corresponding samples in actual physical space.
Figure 6A:
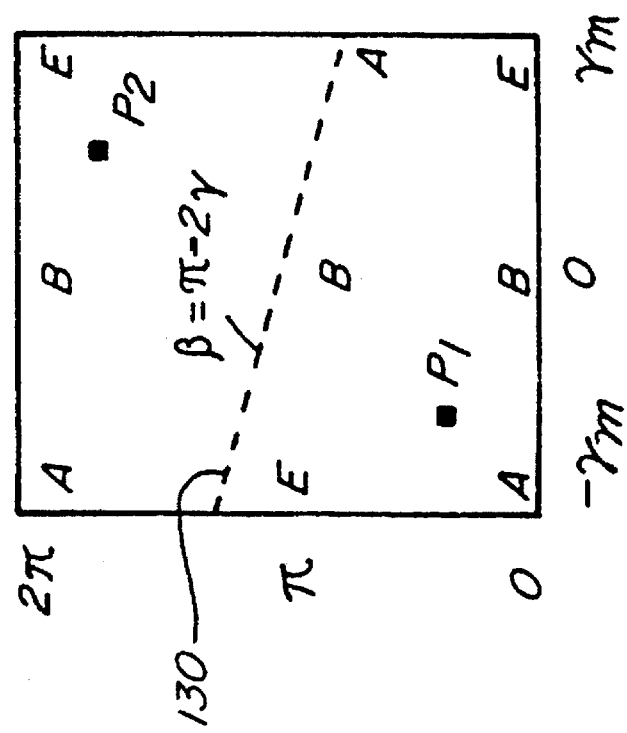

If the POR 130 is selected so that it overlaps the line AE which separates the two half scans the entire Radon space is now divided into two half scan regions as shown in FIG. 6a. The two points, $p_1$ and $p_2$ in FIG. 6a, represent arbitrary redundant sample pairs in the scan. A top-down view of the corresponding samples in the actual physical space is shown in FIG. 6b. The POR is tilted only slightly from the nominal position. The worst case for the tilting occurs when a 10 mm slice thickness is used. Under this condition, the reconstruction plane is rotated only 0.3 degree with respect to the conventional POR.

For the following discussion, $z_1$ and $z_2$ denote the z axis coordinates of the point pair $p_1$ and $p_2$, respectively. Further, the intersections of the POR 130 are denoted with two lines parallel to the z-axis passing through the point pair by $z_{\gamma 1}$ and $z_{\gamma 2}$. Following the operation of linear interpolation, the weighting factor, $w_1$, for point $p_1$ is:

$$w_1 = (z_2 - z_{\gamma 2})/((z_2 - z_{\gamma 2}) + (z_{\gamma 1} - z_1)). \quad (2)$$

Similarly, the weighting factor, $w_2$, for point $p_2$ is:

$$w_2 = (z_{\gamma 1} - z_1)/((z_2 - z_{\gamma 2}) + (z_{\gamma 1} - z_1)). \quad (3)$$

Considering the fact that both the patient and the gantry move at constant speeds, the table position z is proportional to the objection angle $\beta$ Therefore:

$$w_1 = (\beta_2 - \beta_{\gamma 2})/(\beta_2 - \beta_1 + \beta_{\gamma 1} - \beta_{\gamma 2}). \quad (4)$$

In order for two sampling points to form a complementary sampling pair, the following relationship has to exist: $\beta_2 = \beta_1 + \pi + 2\gamma_1$. Considering the fact that the POR 130 is defined by $\beta = \pi + 2\gamma$, then:

$$w_1 = \beta_1/(\pi - 2\gamma_1). \quad (5)$$

Following the same process, the weighting factor for $p_2$ is:

$$w_2 = (2\pi - \beta_2)/(\pi + 2\gamma_2). \tag{6}$$

At the reconstruction plane. $\beta = \pi - 2\gamma$, both weighting factors equal 1. This indicates that the weighting function is continuous everywhere. Also, the weighting factor approaches zero at both $\beta = 0$ and $\beta = 2\pi$. This is a desired property since the inconsistency in the projections is expected to be worst at both locations. In addition, the range for both equations is [0,1] in their respective domains.

The present weighting function can be expressed as follows:

$$w(\beta,\gamma) = \begin{cases} \dfrac{\beta}{\pi - 2\gamma} & 0 \leq \beta \leq \pi - 2\gamma \\ \dfrac{2\pi - \beta}{\pi + 2\gamma} & \pi - 2\gamma < \beta \leq 2\pi \end{cases} \tag{7}$$

With respect to the noise characteristics of the present algorithm, since the weighting function will be multiplied to the projection on a point by point basis, the noise power, $N(\gamma)$ of $w(\beta, \gamma)$, can be defined as the integration of the weighting function squared along the fi direction. If the scanned object is a uniform phantom of cylindrical shape centered at the iso-center, the noise power will be a measure of noise increase for each channel due to the weighting process. The noise power for the present algorithm is:

$$N_{HI}(\gamma) = \int_0^{2\pi} w^2(\beta,\gamma)d\beta = \tag{8}$$

$$\int_0^{\pi - 2\gamma} (\beta^2/(\pi - 2\gamma)^2)d\beta +$$

$$\int_{\pi - 2\gamma}^{2\pi} (2\pi - \beta)^2/((\pi + 2\gamma)^2)d\beta = (2/3)\pi.$$

The noise power is not a function of $\gamma$ (the detector channel). In other words, the impact of multiplying the projection by $w(\beta, \gamma)$ is uniform across the entire detector. This property is desirable since the noise characteristics should be as homogeneous as possible. On the other hand, the noise power for the HE algorithm can be shown to be:

$$N_{HE}(\gamma) = ((\pi^3 - 8\gamma^3)/(3(\pi + 2\gamma)^2)) + ((\pi^3 + 8\gamma^3)/(3(\pi - 2\gamma)^2)) \tag{9}$$

With the HE algorithm, the noise power is a function of the detector channel. At the iso-center channel ($\gamma = 0$), the noise power measure for both algorithms are identical. As the $\gamma$ increases, the noise power measure for the HE algorithm is always higher than with the present algorithm. This is an indication that the present algorithm will perform slightly better in terms of noise suppression.

As explained above, both the present algorithm and the HE algorithm use projections of $2\pi$ rotations for image reconstruction. The weighting function for the present algorithm, however, is continuous. Therefore, no feathering is required. In addition, the present algorithm has limited the weighting values to be between 0 and 1. This results in a improved performance in terms of noise suppression.

From the foregoing description of various embodiments of the present invention, it is evident that the objects of the invention are attained. Although the invention has been described and illustrated in detail, it is to be clearly understood that the same is intended by way of illustration and example only and is not to be taken by way of limitation. Accordingly, the spirit and scope of the invention are to be limited only by the terms of the appended claims.

What is claimed is:

1. A method of producing a tomographic image of an image object from data acquired in a helical scan, the data collected in a series of fan beam projections at a plurality of gantry angles about a z axis and within an image plane, the fan beam projections including a plurality of data at fan beam angles, said method comprising the steps of:

a) generating a projection data matrix from the data collected in the fan beam projections:

b) identifying a line of interpolation/extrapolation which is represented as a straight line in Radon space and between the first and last views, the line of interpolation/extrapolation not being parallel to the views;

c) creating a weighted projection data matrix using the projection data matrix and relative to the identified plane of interpolation/extrapolation.

2. A method in accordance with claim 1 wherein creating a weighted projection data matrix includes the step of applying the following weighting function to the projection data:

$$w(\beta,\gamma) = \begin{cases} \dfrac{\beta}{\pi - 2\gamma} & 0 \leq \beta \leq \pi - 2\gamma \\ \dfrac{2\pi - \beta}{\pi + 2\gamma} & \pi - 2\gamma < \beta \leq 2\pi \end{cases}$$

3. A method of producing a tomographic image of an image object from data acquired in a helical scan, the data collected in a series of fan beam projections at a plurality of gantry angles about a z axis and within an image plane, the fan beam projections including a plurality of data at fan beam angles, comprising the steps of:

a) generating a projection data matrix from the data collected in the fan beam projections;

b) identifying a plane of interpolation/extrapolation between the first projection plane and the last projection plane, the plane of interpolation/extrapolation not being perpendicular to the z axis;

c) creating a weighted projection data matrix using the projection data matrix and relative to the identified plane of interpolation/extrapolation.

4. A method in accordance with claim 3 wherein creating a weighted projection data matrix includes the step of applying the following weighting function to the projection data:

$$w(\beta,\gamma) = \begin{cases} \dfrac{\beta}{\pi - 2\gamma} & 0 \leq \beta \leq \pi - 2\gamma \\ \dfrac{2\pi - \beta}{\pi + 2\gamma} & \pi - 2\gamma < \beta \leq 2\pi \end{cases}$$

5. A system for of producing a tomographic image of an object, said system comprising means for performing a helical scan of the object and for collecting beam projection data during the helical scan from a series of fan beam projections at a plurality of gantry angles about an axis and within an image plane, said tomographic image system further comprising a data acquisition system configured to:

(a) create a projection data array using the data collected in the helical scan;

(b) create a weighted data array by assigning weights to each data element in the projection data array, the weights being assigned by:

(i) generating a projection data matrix from the data collected in the fan beam projections;

(ii) identifying a plane of interpolation/extrapolation between the first projection plane and the last projection plane, the plane of interpolation/extrapolation not being perpendicular to the z axis;

(iii) creating a weighted projection data matrix using the projection data matrix and relative to the identified plane of interpolation/extrapolation.

6. A system in accordance with claim 5 wherein creating a weighted projection data matrix includes applying the following weighting function to the projection data:

$$w(\beta,\gamma) = \begin{cases} \dfrac{\beta}{\pi - 2\gamma} & 0 \leq \beta \leq \pi - 2\gamma \\ \dfrac{2\pi - \beta}{\pi + 2\gamma} & \pi - 2\gamma < \beta \leq 2\pi \end{cases}$$

* * * * *